(12) United States Patent
Happach

(10) Patent No.: US 6,990,847 B2
(45) Date of Patent: Jan. 31, 2006

(54) SENSOR UNIT COMPRISING AN AIR HUMIDITY SENSOR AND AN AIR TEMPERATURE SENSOR

(75) Inventor: Elmar Happach, Stuttgart (DE)

(73) Assignee: sitronic Ges. für elektrotechnische Ausrüstung mbH & Co. KG, Gärtringen (DE)

( * ) Notice: Subject to any disclaimer, the term of this patent is extended or adjusted under 35 U.S.C. 154(b) by 89 days.

(21) Appl. No.: 10/399,354

(22) PCT Filed: Oct. 14, 2001

(86) PCT No.: PCT/DE01/03892

§ 371 (c)(1),
(2), (4) Date: Aug. 14, 2003

(87) PCT Pub. No.: WO02/33395

PCT Pub. Date: Apr. 25, 2002

(65) Prior Publication Data

US 2004/0007049 A1    Jan. 15, 2004

(30) Foreign Application Priority Data

Oct. 18, 2000    (DE) ................................. 100 51 558

(51) Int. Cl.
*G01N 19/10* (2006.01)
(52) U.S. Cl. .................................................. 73/29.02
(58) Field of Classification Search ............. 73/335.04, 73/29.02; 324/664, 689; 204/400, 408, 204/409, 430
See application file for complete search history.

(56) References Cited

U.S. PATENT DOCUMENTS

| | | | |
|---|---|---|---|
| 4,649,364 A | | 3/1987 | Tanahashi et al. |
| 5,345,821 A | * | 9/1994 | Reich et al. ............. 73/335.04 |
| 5,372,427 A | * | 12/1994 | Padovani et al. ........... 374/185 |
| 5,814,726 A | | 9/1998 | Mitter |

FOREIGN PATENT DOCUMENTS

| | | |
|---|---|---|
| DE | 28 51 686 A1 | 6/1979 |
| DE | 40 35 371 A1 | 5/1992 |
| DE | 39 11 812 C2 | 9/1996 |
| DE | 197 29 697 C1 | 2/1999 |
| DE | 197 50 123 A1 | 6/1999 |
| DE | 198 06 041 A1 | 8/1999 |

OTHER PUBLICATIONS

Demisch, Ullrich, DE 40 35 371 C2, Jul. 14, 1994, with Derwent Abstract in English.*

* cited by examiner

Primary Examiner—Charles Garber
(74) Attorney, Agent, or Firm—Walter A. Hackler

(57) ABSTRACT

A sensor unit comprises a mounting base (1) on which an air moisture sensor (3) and an air temperature sensor (4) are disposed. The air moisture sensor (3) is disposed over a bore (5) of the mounting base and covers the bore (5) at least partially. An intensive thermal coupling between the air moisture sensor (3), air temperature sensor (4) and air mixture to be analysed is produced.

3 Claims, 2 Drawing Sheets

SENSOR UNIT COMPRISING AN AIR HUMIDITY SENSOR AND AN AIR TEMPERATURE SENSOR

TECHNICAL FIELD

The invention concerns a sensor unit comprising an air moisture sensor for measuring the relative moisture in the air and an air temperature sensor for measuring the air temperature. If heat is removed from a gaseous medium, e.g. water vapor, the medium is condensed into a liquid, e.g. water, at a corresponding temperature. This temperature is called condensation point or dew point and can be calculated from the measured relative air moisture and the measured air temperature. Sensor units of this type are used in many fields of technology, in particular as condensation protection.

PRIOR ART

A sensor unit comprising an air moisture sensor for measuring the relative air moisture and an air temperature sensor for measuring the air temperature is disclosed e.g. in DE-PS 197 29 697 C1. In contrast to direct determination of the dew point through condensation—as by means of the dew point level on the basis of which condensation on a high-polish surface is observed—it is also possible to determine the dew point without direct measurement through using a calculating method which is not explained in detail herein.

To form the air moisture sensor for measuring the relative air moisture, the capacity between two electrically conducting electrodes is conventionally measured using a polymer layer as dielectric. The dielectric constant of the polymer layer is the measure for the relative moisture.

The air temperature is detected in the vicinity of the air moisture sensor through an air temperature sensor which may be e.g. a temperature-dependent resistance.

Due to the fact that the relative air moisture depends directly on the air temperature for a given water content, the air temperature at the air moisture sensor and at the air temperature sensor should be identical or the temperature deviation must be considered when calculating the dew point. The different mounting technology and structural shapes of known air moisture sensors and the known air temperature sensor produces a temperature difference between both sensors which must be considered for determining the dew point.

DE 40 35 371 A1 describes an integrated structure of such a sensor unit in thin layer technology.

OBJECT OF THE INVENTION

It is the underlying purpose of the present invention to produce an intensive thermal coupling with small temperature difference between air moisture sensor, air temperature sensor and air mixture to be analysed without having to use demanding thin layer technology.

SUBJECT MATTER AND ADVANTAGES OF THE INVENTION

This object is achieved by a sensor unit with common mounting base for the two sensors, an air moisture sensor and an air temperature sensor, wherein the mounting base is provided with a thermally conducting layer to which the air moisture sensor and the air temperature sensor are connected. A conventional conductor plate of a non-conducting or an only slightly conducting material, such as plastic material, can be used.

The air moisture sensor can be disposed above a bore of the mounting base and at least partially cover the bore. The bore improves the accessibility of the air moisture sensor since the air mixture to be analysed can flow to or around the air moisture sensor, i.e. an active sensor surface, via the bore. The cooperation between air mixture and air moisture sensor is optimised. The bore may be metallized to improve the thermal conductivity. The heat or temperature compensation between air moisture sensor and air mixture may take place via a larger accessible contact surface of the air moisture sensor. The temperature difference between the air moisture sensor and the carrier material of the sensors (mounting base) can be reduced in particular when the gas exchange is increased to prevent a temperature difference from the air temperature sensor.

In a preferred sensor unit, the air moisture sensor is formed as capacitive, flat structural element, preferably in SMD technology, and connected via flat contacts with the thermally conducting coating of the mounting base. This further improves exchange between mounting base, air moisture sensor and air temperature sensor.

In a further improvement, the air temperature sensor is disposed in the direct vicinity of the air moisture sensor. This reduces the errors in the calculation of the dew point from the measured variables, temperature and relative air moisture.

The thermal conductivity of the bore can be improved by providing the inner surfaces of the bore with a thermally conducting coating, preferably of metal.

If the housing of the sensor has air passage openings disposed opposite to the bore, the air to be analysed is supplied to the air moisture sensor in an aimed fashion. As far as possible, heat exchange occurs only with the air moisture sensor and the air temperature sensor. Falsification of the measurement through contact between air and further structural elements of the sensor is prevented.

Soldered joints of the sensors with the metal coating or lamination of the mounting base additionally increase the thermal coupling.

To protect the sensor unit from environmental influences, a casing as a protection against climate influence may be added to the carrier material. It can be realized on one or both sides from climate-permeable material. If the casing is climate-permeable only on one side, the second protective element can be realized from any material which is not climate-permeable.

DRAWING

One embodiment of the inventive sensor unit is shown in the schematic drawing and explained in more detail in the following description of the drawing.

DESCRIPTION OF THE EMBODIMENT

Figure 1:
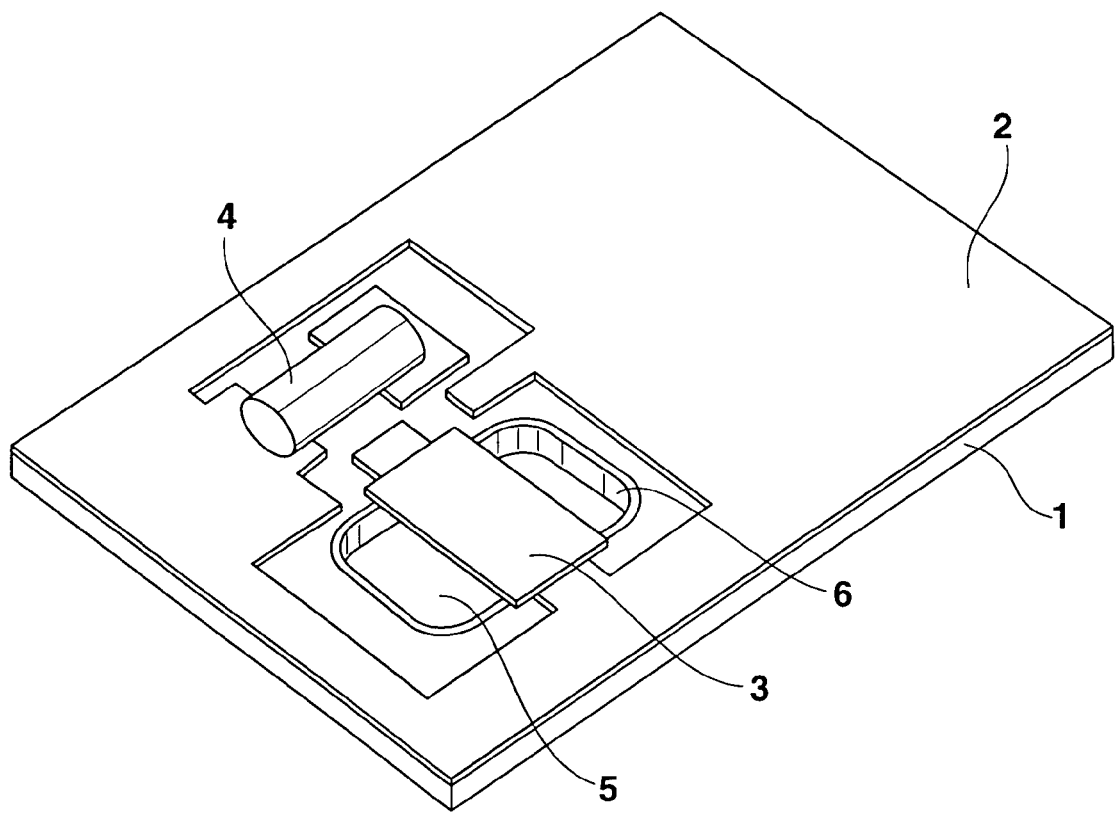
FIG. 1 shows a perspective view of the sensor side, facing away from the air flow, of a sensor unit according to the teaching of the invention.

FIG. 1 shows that a mounting base 1 (printed circuit board) consists of a thermally non-conducting or only little conducting plastic material comprising a thermally conducting coating 2 on the surface. The coating 2 is only schematically indicated in FIG. 1 and has the function of providing good thermal transfer between the structural parts of the mounting base 1 in addition to the switching function. An air moisture sensor 3 for measuring the relative air moisture and an air temperature sensor 4 for measuring the air temperature of the air to be analysed are disposed on the mounting base 1. The mounting base 1 is part of a sensor unit for determining the dew point. Further structural elements located on the mounting base 1 are not shown for clearness.

The air moisture sensor 3 comprises two electrically conducting electrodes between which a polymer is located as dielectric. The dielectric properties of the polymer are influenced by the air moisture. There is a clear connection between the relative air moisture and the water molecularly absorbed by the polymer. The air temperature sensor 4 is formed by a temperature-dependent resistance. It is therefore possible to calculate the dew point by means of the capacity measurement at the air moisture sensor 3 and the resistance measurement at the air temperature sensor 4.

The air temperature sensor 4 is mounted on one of the two sides of the mounting base 1 in the direct vicinity of the air moisture sensor 3 such that the temperature difference between the two sensors 3 and 4 is minimized. The air temperature sensor 4 which is designed as surface-mounted structural element is thermally contacted by a flat solder on the mounting base 1 or on the coating 2. A flat good contact with the coating 2 is provided. The sensors 3 and 4 are in thermal mutual contact via the thermally conducting coating 2.

The air moisture sensor 3 is designed as structural component which can be mounted to the surface in SMD technology ("surface mounted device"). If the active side of the air moisture sensor 3 faces a cavity or through-bore 5 and the metallic coating 2 of the mounting base 1, through-contacts in the base material of the air moisture sensor 3 can be omitted. Mounting technology is facilitated. The air moisture sensor 3 is in thermal contact with the coating 2 of the mounting base 1 through direct soldering of the flat contacts.

To reduce the temperature difference with the surrounding air or gas mixture, the air moisture sensor 3 is disposed with its active side over the cavity or bore 5 in the mounting base 1 such that even with increased gas exchange speeds, only a small temperature difference between air moisture sensor 3 and coating 2 is possible. This can be even assisted through a thermally conducting coating 6 of the cavity 5 so that there is no increased temperature difference between the air temperature and air moisture sensor. The cavity or the bore 5 meets the function of uniformly subjecting an as large as possible surface, i.e. if possible the entire active side of the air moisture sensor 3, to the air mixture. The cavity or bore 5 forms, together with corresponding air slots in the housing of the sensor unit, a flow aid to guide the air mixture to be analysed to the air moisture sensor 3 in an aimed fashion. The coated contact surfaces 6 of the cavity or bore produce a heat exchange between the air mixture and mounting base 1. The surface proportions for the heat exchange between air mixture and air moisture sensor 3 or mounting base 1 and air temperature sensor 4 are approximately equal and are coordinated such that almost identical heat amounts are transferred to the sensors 3 and 4. The air moisture sensor 3 is heated or cooled at the active electrode via the air and the air temperature sensor 4 is heated or cooled via the coating 6 and the coating 2 is heated or cooled between air temperature sensor 4 and air moisture sensor 3.

Figure 2:
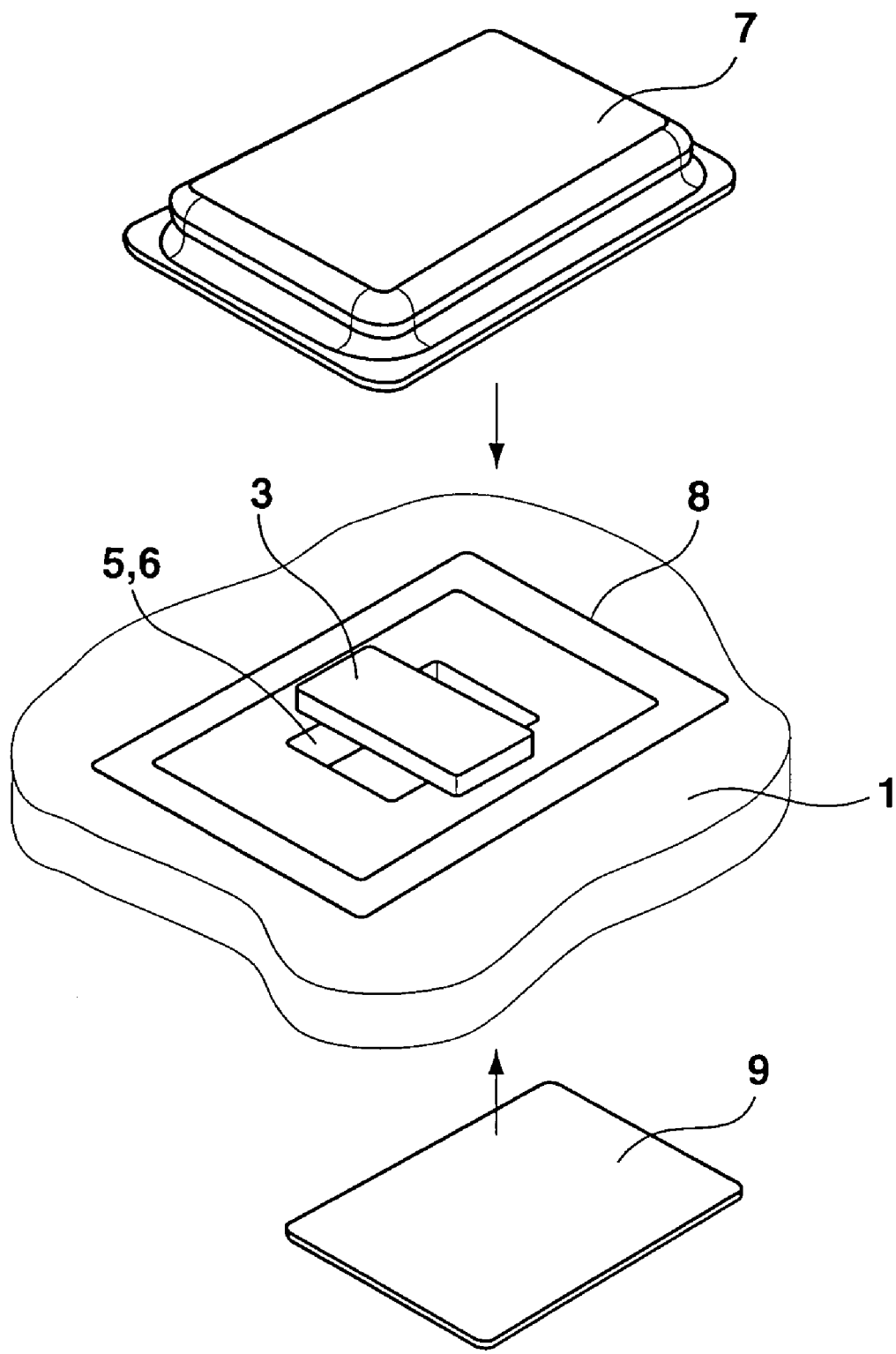
FIG. 2 shows a perspective view of a climate casing of the sensor unit of FIG. 1.

The air moisture sensor 3 can be covered on the side opposite to the sensor with a climate-permeable diaphragm 9. The climate casing can be provided on the sensor side and be made from any material. Preferably, a metal lid 7 in SMD soldering technology is disposed on a partial region 8 to further reduce the temperature difference (FIG. 2).

List of Reference Numerals

| | |
|---|---|
| 1 | Mounting base |
| 2 | coating |
| 3 | air moisture sensor |
| 4 | air temperature sensor |
| 5 | cavity or bore |
| 6 | coating |
| 7 | metal lid |
| 8 | partial region |
| 9 | diaphragm |

What is claimed is:

1. A sensor unit comprising:
   a mounting base;
   an air moisture sensor disposed over a bore in the mounting base, inner surfaces of the bore being provided with thermally conducting coating;
   a separate air temperature sensor disposed on the mounting base; and
   a separate thermally conducting coating, disposed on the mounting base, for connecting the air moisture sensor and the air temperature sensor in order to provide thermal contact between the two separate sensors.

2. The senor unit according to claim 1 further comprising a casing for receiving the sensor unit, the casing having air passage openings disposed opposite the bore.

3. The sensor unit according to claim 1 further comprising a climate permeable casing disposed on an opposite side of the air moisture sensor.

* * * * *

UNITED STATES PATENT AND TRADEMARK OFFICE
CERTIFICATE OF CORRECTION

PATENT NO. : 6,990,847 B2
DATED : January 31, 2006
INVENTOR(S) : Elmar Hoppach

It is certified that error appears in the above-identified patent and that said Letters Patent is hereby corrected as shown below:

<u>Title page,</u>
Item [75], Inventor, should read -- Elmar Hoppach, Stuttgart (DE) --.

Signed and Sealed this

Second Day of May, 2006

JON W. DUDAS
*Director of the United States Patent and Trademark Office*